United States Patent
Geyer et al.

(10) Patent No.: US 10,328,093 B2
(45) Date of Patent: Jun. 25, 2019

(54) ANTHRACYCLINE FORMULATIONS

(71) Applicant: CYTRX CORPORATION, Los Angeles, CA (US)

(72) Inventors: Scott Geyer, Oakland, CA (US); Daniel Levitt, San Francisco, CA (US); Carrie Nodgaard, Los Angeles, CA (US); Edward H. Trappler, Langhorne, PA (US)

(73) Assignee: CytRx Corporation, Los Angeles, CA (US)

( * ) Notice: Subject to any disclaimer, the term of this patent is extended or adjusted under 35 U.S.C. 154(b) by 0 days.

(21) Appl. No.: 15/590,331

(22) Filed: May 9, 2017

(65) Prior Publication Data

US 2017/0340655 A1 Nov. 30, 2017

Related U.S. Application Data

(63) Continuation of application No. 14/651,898, filed as application No. PCT/US2013/075002 on Dec. 13, 2013.

(60) Provisional application No. 61/737,003, filed on Dec. 13, 2012.

(51) Int. Cl.
| | | |
|---|---|---|
| *A61K 9/00* | (2006.01) | |
| *A61K 9/19* | (2006.01) | |
| *A61K 47/26* | (2006.01) | |
| *A61K 31/704* | (2006.01) | |
| *A61K 31/7056* | (2006.01) | |

(52) U.S. Cl.
CPC .......... *A61K 31/704* (2013.01); *A61K 9/0019* (2013.01); *A61K 9/19* (2013.01); *A61K 31/7056* (2013.01); *A61K 47/26* (2013.01)

(58) Field of Classification Search
CPC .............. A61K 31/704; A61K 31/7056; A61K 9/0019; A61K 9/19; A61K 47/26
See application file for complete search history.

(56) References Cited

U.S. PATENT DOCUMENTS

| | | | |
|---|---|---|---|
| 4,840,938 A | 6/1989 | Gatti et al. | |
| 7,387,771 B1 | 6/2008 | Kratz | |
| 7,902,144 B2 | 3/2011 | Kratz | |
| 8,703,724 B2 | 4/2014 | Kratz | |
| 2001/0036444 A1 | 11/2001 | Placke et al. | |
| 2003/0013666 A1 | 1/2003 | Gatti et al. | |
| 2005/0148534 A1 | 7/2005 | Castellino et al. | |
| 2010/0172844 A1 | 7/2010 | Neri et al. | |
| 2012/0135914 A1* | 5/2012 | Demeule ................ | A61K 31/04 514/1.3 |

FOREIGN PATENT DOCUMENTS

| | | |
|---|---|---|
| EP | 2 216 049 A1 | 8/2010 |
| JP | H07-076515 A | 3/1995 |
| JP | 2010-526845 A | 8/2010 |
| WO | WO-02/43765 A2 | 6/2002 |
| WO | WO-2008/138646 A1 | 11/2008 |

OTHER PUBLICATIONS

Kratz, F., J. Controlled Rel., 2008, 132, p. 171-183. (Year: 2008).*
Sanchez et al., Clin. Cancer Res., Published OnlineFirst May 22, 2012. (Year: 2012).*
Sanchez, et al., "Anti-Myeloma Effects of the Novel Anthracycline Derivative INNO-206", Blood 118(21): Abstract 5107, 53rd Annual Meeting of the American Society of Hematology (2011).
Bartzatt et al., "Analysis for doxorubicin by spectrophotometry and reversed phase high performance liquid chromatography (HPLC)," Current Topics in Analytical Chemistry, 9:63-69 (2012).
Kaneko et al., "New hydrazone derivatives of adriamycin and their immunoconjugates—a correlation between acid stability and cytotoxicity," Bioconjugates Chem, 2:133-141 (1991).
Kratz et al., "Drug-polymer conjugates containing acid-cleavable bonds," Crit Rev Ther Drug Carrier Syst., 16:245-88 (1999).
Kratz et al., "Acute and repeat-dose toxicity studies of the (6-maleimidocaproyl)hydrazine derivative of doxorubicin (DOXO-EMCH), an albumin-binding prodrug of the anticancer agent doxorubicin," Hum Exp Toxicol, 26:19-35 (2007).
Kratz et al., "Probing the cysteine-34 position of endogenous serum albumin with thiol-binding doxorubicin derivatives. Improved efficacy of an acid-sensitive doxorubicin derivative with specific albumin-binding properties compared to that of the parent compound," J Med Chem, 45:5523-5533 (2002).
Maeda et al., "Tumor vascular permeability and the EPR effect in macromolecular therapeutics: a review," J Control Release, 65:271-284 (2000).
Official Monographs, pp. 4564-4565, The United States Pharmacopeia 35, US Pharmacopeial Convention (2012).
Shalaev , The Impact of Buffer on Processing and Stability of Freeze-Dried Dosage Forms, Part 1: Solution Freezing Behavior, Pharmaceuticals Sciences, Pfizer Global Research & Development (Abstract).

(Continued)

*Primary Examiner* — Jonathan S Lau
(74) *Attorney, Agent, or Firm* — Sheridan Ross P.C.

(57) ABSTRACT

The invention relates to reconstituted formulations comprising an anthracycline compound, ethanol, and water. The invention also relates to injectable compositions comprising the reconstituted formulation and Lactated Ringer's solution. Additionally, the invention relates to methods of using the formulations and compositions.

39 Claims, No Drawings

(56) References Cited

OTHER PUBLICATIONS

Unger et al., "Phase I and pharmacokinetic study of the (6-maleimidocaproyl)hydrazine derivative of doxorubicin," Clin Cancer Res, 13:4858-4866 (2007).
Willner et al., "(6-Maleimidocaproyl)hydrazone of doxorubicin—a new derivative for the preparation of immunoconjugates of doxorubicin," Bioconjugate Chem, 4:521-527 (1993).
The Japanese Pharmacopoeia, 16$^{th}$ Ed., Preparations for Injection, p. 13 (Mar. 24, 2011).

* cited by examiner

ANTHRACYCLINE FORMULATIONS

CROSS REFERENCE TO RELATED APPLICATIONS

This application is a continuation application of U.S. patent application Ser. No. 14/651,898, filed Jun. 12, 2015, which is a national stage application under 35 U.S.C. § 371 of International Application No. PCT/US2013/075002, filed Dec. 13, 2013, which claims priority from U.S. Provisional Application 61/737,003, filed Dec. 13, 2012. The disclosure of each of these referenced applications is incorporated by reference herein in their entireties.

BACKGROUND OF THE INVENTION

Anthracyclines are a class of antibiotics derived from certain types of *Streptomyces* bacteria. Anthracyclines are often used as cancer therapeutics and function in part as nucleic acid intercalating agents and inhibitors of the DNA repair enzyme topoisomerase II, thereby damaging nucleic acids in cancer cells, preventing the cells from replicating. One example of an anthracycline cancer therapeutic is doxorubicin, which is used to treat a variety of cancers including breast cancer, lung cancer, ovarian cancer, lymphoma, and leukemia. The 6-maleimidocaproyl hydrazone of doxorubicin (DOXO-EMCH) was originally synthesized to provide an acid-sensitive linker that could be used to prepare immunoconjugates of doxorubicin and monoclonal antibodies directed against tumor antigens (Willner et al., Bioconjugate Chem 4:521-527 (1993)). In this context, antibody disulfide bonds are reduced with dithiothreitol to form free thiol groups, which in turn react with the maleimide group of DOXO-EMCH to form a stable thioether bond. When administered, the doxorubicin-antibody conjugate is targeted to tumors containing the antigen recognized by the antibody. Following antigen-antibody binding, the conjugate is internalized within the tumor cell and transported to lysosomes. In the acidic lysosomal environment, doxorubicin is released from the conjugate intracellularly by hydrolysis of the acid-sensitive hydrazone linker. Upon release, the doxorubicin reaches the cell nucleus and is able to kill the tumor cell. For additional description of doxorubicin and DOXO-EMCH see, for example, U.S. Pat. Nos. 7,387,771 and 7,902,144 and U.S. patent application Ser. No. 12/619,161, each of which are incorporated in their entirety herein by reference.

A subsequent use of DOXO-EMCH was developed by reacting the molecule in vitro with the free thiol group (Cys-34) on human serum albumin (HSA) to form a stable thioether conjugate with this circulating protein (Kratz et al., J Med Chem 45:5523-5533 (2002)). Based on these results, it was hypothesized that intravenously-administered DOXO-EMCH would rapidly conjugate to HSA in vivo and that this macromolecular conjugate would preferentially accumulate in tumors due to an "enhanced permeability and retention" (EPR) intratumor effect (Maeda et al., J Control Release 65:271-284 (2000)).

Acute and repeat-dose toxicology studies with DOXO-EMCH in mice, rats, and dogs identified no toxicity beyond that associated with doxorubicin, and showed that all three species had significantly higher tolerance for DOXO-EMCH compared to doxorubicin (Kratz et al., Hum Exp Toxicol 26:19-35 (2007)). Based on the favorable toxicology profile and positive results from animal tumor models, a Phase 1 clinical trial of DOXO-EMCH was conducted in 41 advanced cancer patients (Unger et al., Clin Cancer Res 13:4858-4866 (2007)). This trial found DOXO-EMCH to be safe for clinical use. In some cases, DOXO-EMCH induced tumor regression.

Due to the sensitivity of the acid-cleavable linker in DOXO-EMCH, it is desirable to have formulations that are stable in long-term storage and during reconstitution (of, e.g., previously lyophilized compositions) and administration. DOXO-EMCH, when present in compositions, diluents and administration fluids used in current formulations, is stable only when kept at low temperatures. The need to maintain DOXO-EMCH at such temperatures presents a major problem in that it forces physicians to administer cold (4° C.) DOXO-EMCH compositions to patients. Maintaining DOXO-EMCH at low temperatures complicates its administration in that it requires DOXO-EMCH to be kept at 4° C. and diluted at 4° C. to prevent degradation that would render it unsuitable for patient use. Further, administration at 4° C. can be harmful to patients whose body temperature is significantly higher (37° C.).

Lyophilization has been used to provide a stable formulation for many drugs. However, reconstitution of lyophilized DOXO-EMCH in a liquid that does not maintain stability at room temperature can result in rapid decomposition of DOXO-EMCH. Use of an inappropriate diluent to produce an injectable composition of DOXO-EMCH can lead to decreased stability and/or solubility. This decreased stability manifests itself in the cleavage of the linker between the doxorubicin and EMCH moieties, resulting in degradation of the DOXO-EMCH into two components: doxorubicin and linker-maleimide. Thus, stable, reconstituted lyophilized solutions of anthracycline-EMCH (e.g., DOXO-EMCH), and injectable compositions containing the same, are required to solve these problems and to provide a suitable administration vehicle that can be used reasonably in treating patients both for clinical trials and commercially.

SUMMARY OF THE INVENTION

The present invention provides reconstituted formulations and injectable compositions of anthracycline compounds.

For example, the invention provides a reconstituted formulation comprising an anthracycline compound and a reconstitution liquid, wherein the reconstituted formulation is prepared by reconstituting a lyophilized composition of the anthracycline compound in a reconstitution liquid comprising ethanol and water. An exemplary reconstituted formulation comprises DOXO-EMCH and a reconstitution liquid.

In some embodiments, the volume:volume ratio of ethanol:water in a reconstituted formulation of the invention is about 10:90 to about 90:10, for example, about 40:60 to about 60:40, about 45:55 to about 55:45, or about 50:50.

In some embodiments, the concentration of anthracycline compound in a reconstituted formulation is from about 1 mg/ml to about 30 mg/ml, for example, from about 5 mg/ml to about 25 mg/ml. In certain embodiments, the concentration of anthracycline compound in the reconstituted formulation is about 10 mg/ml.

The invention also provides an injectable composition of an anthracycline compound comprising a reconstituted formulation (as described above) and Lactated Ringer's solution. An exemplary injectable composition comprises DOXO-EMCH, a reconstitution liquid, and Lactated Ringer's solution.

In some embodiments, the concentration of anthracycline compound in the injectable composition is from about 0.1 mg/ml to about 25 mg/ml, for example from about 7 mg/ml to about 17 mg/ml, from about 0.1 mg/ml to about 5 mg/ml, or from about 0.25 mg/ml to about 4.5 mg/ml. In certain embodiments, the concentration of the anthracycline compound in the injectable composition is about 2.4 mg/ml.

The invention further provides a reconstituted formulation or injectable composition as described above for use in treating cancer in a patient. The cancer may be selected from the following non-limiting examples: a solid tumor cancer, breast cancer, lung cancer, endometrial cancer, ovarian cancer, pancreatic cancer, cancer of the adrenal cortex, non-Hodgkin's lymphoma, multiple myeloma, leukemia, Kaposi's sarcoma, Ewing's sarcoma, soft tissue sarcoma, nephroblastoma, glioblastoma, prostate cancer, liver cancer, bone cancer, chondrosarcoma, renal cancer, bladder cancer, and gastric cancer. In certain embodiments, the cancer is selected from: a solid tumor cancer and a soft tissue sarcoma. In particular embodiments, the pancreatic cancer is pancreatic ductal adenocarcinoma.

The invention provides the use of a reconstituted formulation or injectable composition as described above in the manufacture and administration of a medicament for treating cancer in a patient. The cancer may be selected from the following non-limiting examples: a solid tumor cancer, breast cancer, lung cancer, endometrial cancer, ovarian cancer, pancreatic cancer, cancer of the adrenal cortex, non-Hodgkin's lymphoma, multiple myeloma, leukemia, Kaposi's sarcoma, Ewing's sarcoma, soft tissue sarcoma, nephroblastoma, glioblastoma, prostate cancer, liver cancer, bone cancer, chondrosarcoma, renal cancer, bladder cancer, and gastric cancer. In certain embodiments, the cancer is selected from: a solid tumor cancer and a soft tissue sarcoma. In particular embodiments, the pancreatic cancer is pancreatic ductal adenocarcinoma.

The invention also provides a method for treating cancer in a patient, comprising administering (e.g., intravenously) a reconstituted formulation or injectable composition as described above to a patient. The cancer may be selected from the following non-limiting examples: a solid tumor cancer, breast cancer, lung cancer, endometrial cancer, ovarian cancer, pancreatic cancer, cancer of the adrenal cortex, non-Hodgkin's lymphoma, multiple myeloma, leukemia, Kaposi's sarcoma, Ewing's sarcoma, soft tissue sarcoma, nephroblastoma, glioblastoma, prostate cancer, liver cancer, bone cancer, chondrosarcoma, renal cancer, bladder cancer, and gastric cancer. In certain embodiments, the cancer is selected from: a solid tumor cancer and a soft tissue sarcoma. In particular embodiments, the pancreatic cancer is pancreatic ductal adenocarcinoma.

The invention also provides a method of preparing a reconstituted formulation of an anthracycline compound (e.g., DOXO-EMCH), comprising reconstituting a lyophilized composition of the anthracycline compound in a reconstitution liquid comprising ethanol and water. In certain embodiments, the volume:volume ratio of ethanol:water is about 10:90 to about 90:10, for example, about 40:60 to about 60:40, about 45:55 to about 55:45, or about 50:50. In some embodiments, the concentration of the anthracycline compound in the reconstituted formulation useful in the method is from about 1 mg/ml to about 30 mg/ml, for example, from about 5 mg/ml to about 25 mg/ml. In certain embodiments, the concentration of the anthracycline compound in the reconstituted formulation is about 10 mg/ml.

In some embodiments, the invention provides a method of preparing an injectable composition of an anthracycline compound comprising diluting a reconstituted formulation as described above with Lactated Ringer's solution. In certain embodiments, the concentration of the anthracycline compound in the injectable composition is from about 1 mg/ml to about 25 mg/ml, for example, from about 1 mg/ml to about 5 mg/ml or from about 7 mg/ml to about 17 mg/ml.

DETAILED DESCRIPTION OF THE INVENTION

Unless otherwise defined herein, scientific and technical terms used in this application shall have the meanings that are commonly understood by those of ordinary skill in the art. Generally, nomenclature used in connection with, and techniques of, chemistry, molecular biology, cell and cancer biology, immunology, microbiology, pharmacology, and protein and nucleic acid chemistry, described herein, are those well known and commonly used in the art.

All publications, patents and published patent applications referred to in this application are specifically incorporated by reference herein. In case of conflict, the present specification, including its specific definitions, will control.

Throughout this specification, the word "comprise" or variations such as "comprises" or "comprising" will be understood to imply the inclusion of a stated integer (or components) or group of integers (or components), but not the exclusion of any other integer (or components) or group of integers (or components).

The singular forms "a," "an," and "the" include the plurals unless the context clearly dictates otherwise.

The term "including" is used to mean "including but not limited to." "Including" and "including but not limited to" are used interchangeably.

An "anthracycline" refers to a member of a class of antibiotics produced by *Streptomyces peucetius* and/or *Streptomyces coerulubidus*. Exemplary anthracyclines include, but are not limited to, doxorubicin, daunorubicin, epirubicin, idarubicin, valrubicin, pirarubicin, zorubicin, aclarubicin, caminomycin, mitoxantrone, and ametantrone.

As used herein, "Lactated Ringer's solution" (LR) refers to a sterile solution of sodium chloride, potassium chloride, calcium chloride, and sodium lactate in sterile water for injection. A 100 mL of solution of LR generally contains between 285.0 mg and 315.0 mg of sodium, between 14.2 mg and 17.3 mg of potassium, between 4.90 mg and 6.00 mg of calcium, between 368.0 mg and 408.0 mg of chloride, and between 231.0 mg and 261.0 mg of lactate. LR does not contain antimicrobial agents. The pH of the Lactated Ringer's solution is generally between 6 and 8. Lactated Ringer's solution is described in USP 35, Official Monographs, pgs. 4564-4565 (2012), incorporated in its entirety herein by reference.

The terms "patient" and "individual" are used interchangeably and refer to either a human or a non-human animal. These terms include mammals such as humans, primates, livestock animals (e.g., bovines, porcines), companion animals (e.g., canines, felines) and rodents (e.g., mice and rats).

The term "pharmaceutically acceptable carrier" refers to a non-toxic carrier that may be administered to a patient, together with an anthracycline compound of this invention, and which does not destroy the pharmacological activity of the anthracycline. The term "excipient" refers to an additive in a formulation or composition that is not a pharmaceutically active ingredient.

The term "pharmaceutically effective amount" refers to an amount effective to treat cancer in a patient, e.g., effecting a beneficial and/or desirable alteration in the general health of a patient suffering from a disease (e.g., cancer). The skilled worker will recognize that treating cancer includes, but is not limited to, killing cancer cells, preventing the growth of new cancer cells, causing tumor regression (a decrease in tumor size), causing a decrease in metastasis, improving vital functions of a patient, improving the well-being of the patient, decreasing pain, improving appetite, improving the patient's weight, and any combination thereof. A "pharmaceutically effective amount" also refers to the amount required to improve the clinical symptoms of a patient. The therapeutic methods or methods of treating cancer described herein are not to be interpreted or otherwise limited to "curing" cancer.

Unless otherwise specified, it is to be understood that each embodiment of the invention may be used alone or in combination with any one or more other embodiments of the invention.

Compounds of the Invention

Anthracycline compounds useful in the formulations, compositions, and methods of the invention are described by the following schematic, wherein the anthracycline compound comprises an anthracycline, a linker molecule, and at least one protein-binding molecule, and wherein "X" represents a cleavable bond.

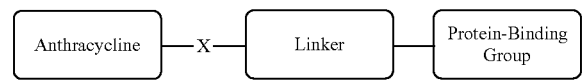

Exemplary anthracyclines include, but are not limited to, doxorubicin, daunorubicin, epirubicin, idarubicin, valrubicin, pirarubicin, zorubicin, aclarubicin, caminomycin, mitoxantrone, and ametantrone. In some embodiments, the anthracycline is doxorubicin.

In some embodiments, the cleavable bond ("X") is an acid-cleavable bond. Exemplary acid-cleavable bonds include, but are not limited to, acetal, ketal, imine, hydrazone, carboxylhydrazone or sulphonylhydrazone bonds, or cis-aconityl bonds or bonds containing a substituted or unsubstituted trityl group. In certain embodiments, the acid-cleavable bond is a hydrazone bond.

In some embodiments, the linkers of the present invention are organic molecules. Such linkers may comprise an aliphatic carbon chain and/or an aliphatic carbon ring with 1-12 carbon atoms, wherein any of the carbon atoms may be substituted with an —OH or =O, and wherein any of the carbon atoms may be substituted for oxygen atoms where appropriate and chemically feasible. In some embodiments, the aliphatic linker may comprise an alkyl chain comprising 1-12 carbon atoms, an alkenyl chain comprising 2-12 carbon atoms, or an alkynyl chain comprising 2-12 carbon atoms, wherein any of the carbon atoms may be substituted with an —OH or =O, and wherein any of the carbon atoms may be substituted for oxygen atoms where appropriate and chemically feasible. In particular embodiments, the aliphatic linker is an alkyl chain comprising 1-12 carbon atoms, wherein any of the carbon atoms may be substituted with an =O, where appropriate and chemically feasible. In yet other embodiments, the aliphatic linker is an alkyl chain comprising 3-9, 4-8, or 5-7 carbon atoms, wherein any of the carbon atoms may be substituted with an =O, where appropriate and chemically feasible. In a particular embodiment, the aliphatic linker is an alkyl chain comprising 6 carbon atoms, wherein the carbon atom attached to the cleavable bond "X" is substituted with an =O.

In some embodiments, the cleavable bond ("X") is enzyme-cleavable. Exemplary enzyme-cleavable linkers include, but are not limited to, peptide linkers and linkers comprising one or more carbamate bonds. A peptide linker can comprise, for example, 1-5, 1-10, 1-15, 1-20, 1-25, 1-30, 1-35, 1-40, 2-5, 2-10, 2-15, 2-20, 2-25, 2-30, 2-35, or 2-40 amino acid residues. Exemplary peptide linkers include, but are not limited to, linkers comprising 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 amino acid residues. A peptide linker may be designed to be specifically cleavable by one or more proteases. In some embodiments, the bond being cleaved is a peptide bond, an imide bond, or a carboxyl-hydrazone bond.

Exemplary protein-binding groups include, but are not limited to, a maleimide group, a haloacetamide group, a haloacetate group, a pyridyldithio group, an N-hydroxysuccinimide ester group, and an isothiocyanate group. In certain embodiments, the protein-binding group is a maleimide group. Exemplary protein-binding groups also include a disulphide group, a vinylcarbonyl group, an aziridine group or an acetylene group. A disulphide group may be activated by a thionitrobenzoic acid (e.g. 5'-thio-2-nitrobenzoic acid) as the exchangeable group. A maleimide, pyridyldithio, or N-hydroxysuccinimide ester group can, where appropriate, be substituted by an alkyl group or by the above water-soluble groups. In general, a protein-binding group possesses protein-binding properties, i.e., it binds covalently ("a covalent protein-binding group") or noncovalently ("a non-covalent protein-binding group"), in a physiological environment, to particular amino acids on the surface of the protein. The maleimide group, the haloacetamide group, the haloacetate group, the pyridyldithio group, the disulphide group, the vinylcarbonyl group, the aziridine group, and/or the acetylene group preferably reacts with thiol (—SH) groups of cysteines, while the N-hydroxysuccinimide ester group and/or the isothiocyanate group preferably react with the amino group (—NH) of lysines, on the surface of a protein.

The anthracycline compounds of the invention include any and all combinations of one or more anthracyclines, cleavable bonds, linkers, and protein-binding groups. Exemplary anthracycline compounds comprise an anthracycline, an acid-cleavable bond, an alkyl linker, and a covalent protein-binding group. In certain embodiments, the anthracycline compound comprises an anthracycline, a hydrazone bond as the acid-cleavable bond, an alkyl linker, and a maleimide group as the covalent protein-binding group. In other embodiments, the anthracycline compound comprises an anthracycline, a hydrazone bond as the acid-cleavable bond, a 6-carbon alkyl linker wherein the carbon atom attached to the cleavable bond is substituted with an =O, and a maleimide group as the covalent protein-binding group (i.e., an anthracycline-EMCH molecule).

An exemplary compound of the present invention is DOXO-EMCH. The term "DOXO-EMCH," alone or in combination with any other term, refers to a compound as depicted by the following structure:

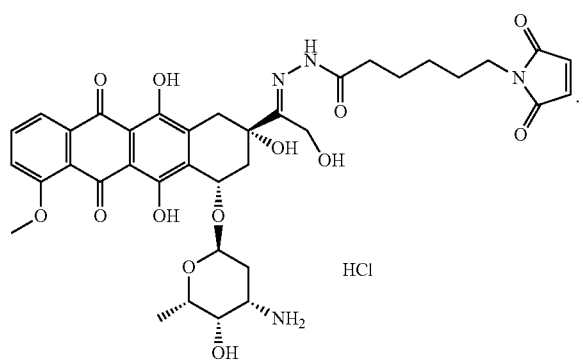 [SMILES: COc1cccc2c1C(=O)c1c(O)c3c(c(O)c1C2=O)C[C@@](O)(/C(CO)=N/NC(=O)CCCCCN1C(=O)C=CC1=O)C[C@@H]3O[C@H]1C[C@H](N)[C@H](O)[C@H](C)O1 ; Cl]

DOXO-EMCH is also referred to as (E)-N'-(1-((2S,4S)-4-(4-amino-5-hydroxy-6-methyl-tetrahydro-2H-pyran-2-yloxy-2,5,12-trihydroxy-7-methoxy-6,11-dioxo1,2,3,4,6,11-hexahydrotetracen-2-yl)-2-hydroxyethylidene)-6-(2,5-dioxo-2H-pyrrol-1(5H)yl)hexanehydrazide•HCl.

The present invention is based on the surprising discoveries that lyophilized DOXO-EMCH is stable when reconstituted in a mixture of ethanol and water after lyophilization, and that it maintains its stability when subsequently diluted in Lactated Ringer's solution. Previous formulations of DOXO-EMCH comprised N-acetyltryptophan, phosphate buffer, and sucrose. Indeed, N-acetyltryptophan was thought to be required to maintain the stability of DOXO-EMCH. However, even in the presence of N-acetyltryptophan, the DOXO-EMCH in those previous formulations degraded at room temperature, resulting in the release of doxorubicin. More specifically, in previous formulations, the imide bond between the doxorubicin and EMCH moieties undergoes acid-catalyzed hydrolysis. Administration of doxorubicin is undesirable because it is more toxic than DOXO-EMCH, especially at concentrations required for the effective treatment of cancer. Further, unlike DOXO-EMCH, doxorubicin is not targeted to tumors. Thus, the provision of formulations that reduce the amount of degradation of anthracycline compounds (e.g., anthracycline-EMCH) to individual components (i.e., anthracycline and EMCH) are of great benefit. In light of the toxicity associated with anthracyclines such as doxorubicin, even a small increase in stability of the anthracycline compound will be of great benefit. The provision of anthracycline compound formulations which both reduce the amount of degradation of anthracycline compounds and allow for reconstitution and administration to patients at room temperature are particularly useful.

Surprisingly, the formulations and compositions of the invention stabilize DOXO-EMCH and produce low amounts of free doxorubicin as a degradation byproduct. This stability is observed even without N-acetyltryptophan. Even more surprisingly, the formulations and compositions of the present invention are stable at room temperature. Previous formulations and compositions were stable only at cold temperatures (e.g., 4° C.), making handling and administration difficult for clinicians. In addition, the required administration of DOXO-EMCH formulations at 4° C. was dangerous for the patients. The formulations and compositions of the present invention eliminate the need for cold handling of the drug product, and allow physicians to administer the drug product at room temperature. Moreover, it was unexpected that a reconstitution liquid of ethanol and water stabilized the DOXO-EMCH. It was also unexpected that a reconstitution liquid of ethanol and water would quickly solubilize the DOXO-EMCH (within less than a minute).

Generally, lyophilized pharmaceutical formulations and compositions are not reconstituted in ethanol and water, likely because ethanol is potentially toxic and must be titrated carefully to avoid intoxication of the patient. Indeed, buffered saline solution is typically used as a reconstitution liquid due to its low toxicity.

Reconstituted Formulations

Lyophilization is often used as a means of storing compounds susceptible to degradation in solution. However, determining a proper liquid in which to reconstitute a lyophilized formulation is not always a straightforward endeavor. Use of an unsuitable reconstitution liquid can negatively impact a compound's stability or solubility, causing its aggregation or degradation. Previously, lyophilized DOXO-EMCH formulations had been reconstituted in a solution of 10 mM sodium phosphate in 5% D-(+)-glucose (pH 6.4) (Unger et al., Clin Cancer Res 13:4858-4866 (2007), Kratz et al., Hum Exp Toxicol 26:19-35 (2007)) or in sterile water for injection. However, these methods were not ideal because they required extensive and prolonged mixing to allow complete solubilization of the drug product which, due to the low stability of DOXO-EMCH in these formulations, left only a short window during which the reconstituted formulation could be used for intravenous administration.

Described herein are improved reconstitution liquids and methods. Surprisingly, reconstitution in a mixture of ethanol and water results in rapid solubilization (a few minutes) as well as enhanced stability of DOXO-EMCH. In some embodiments, the invention provides a reconstituted formulation comprising an anthracycline compound (e.g., DOXO-EMCH) and a reconstitution liquid comprising ethanol and water. In some embodiments, the invention provides a reconstituted formulation consisting of an anthracycline compound (e.g., DOXO-EMCH) and a reconstitution liquid consisting of ethanol and water. The volume:volume ratio of ethanol:water for use as a reconstitution liquid may be from about 10:90 to about 90:10, e.g., about 10:90, about 20:80, about 30:70, about 40:60, about 41:59, about 42:58, about 43:57, about 44:56, about 45:55, about 46:54, about 47:53, about 48:52, about 49:51, about 50:50 (e.g., 50±5:50±5), about 51:49, about 52:48, about 53:47, about 54:46, about 55:45, about 56:44, about 57:43, about 58:42, about 59:41, about 60:40, about 70:30, about 80:20, about 90:10, or any intermediate ratio thereof.

The concentration of anthracycline compound (e.g., DOXO-EMCH) useful in a reconstituted formulation of the invention is any amount of the anthracycline compound that remains stable in the composition. For example, the concentration of the anthracycline compound may be from about 1 mg/ml to about 500 mg/ml in a reconstituted composition. In some embodiments, the concentration of the anthracycline compound may be from about 1 mg/ml to about 100 mg/ml, from about 1 mg/ml to about 30 mg/ml, or from about 5 mg/ml to about 25 mg/ml. In particular embodiments, the concentration of the anthracycline compound may be 1.0±0.5 mg/ml, 2.0±0.5 mg/ml, 3.0±0.5 mg/ml, 4.0±0.5 mg/ml, 5.0±0.5 mg/ml, 6.0±0.5 mg/ml, 7.0±0.5 mg/ml, 8.0±0.5 mg/ml, 9.0±0.5 mg/ml, 10.0±0.5 mg/ml, 11.0±0.5 mg/ml, 12.0±0.5 mg/ml, 13.0±0.5 mg/ml, 14.0±0.5 mg/ml, 15.0±0.5 mg/ml, 16.0±0.5 mg/ml, 17.0±0.5 mg/ml, 18.0±0.5 mg/ml, 19.0±0.5 mg/ml, 20.0±0.5 mg/ml, 21.0±0.5 mg/ml, 22.0±0.5 mg/ml, 23.0±0.5 mg/ml 24.0±0.5 mg/ml, and 25.0±0.5 mg/ml. In some embodiments, the concentration of the anthracycline compound may be from about 1.4 mg/ml to about 3.4 mg/ml, for example, 1.4±0.1 mg/ml, 1.5±0.1 mg/ml, 1.6±0.1 mg/ml, 1.7±0.1 mg/ml, 1.8±0.1 mg/ml, 1.9±0.1 mg/ml, 2.0±0.1 mg/ml, 2.1±0.1 mg/ml, 2.2±0.1 mg/ml, 2.3±0.1 mg/ml, 2.4±0.1 mg/ml, 2.5±0.1 mg/ml, 2.6±0.1 mg/ml, 2.7±0.1 mg/ml, 2.8±0.1 mg/ml, 2.9±0.1 mg/ml, 3.0±0.1 mg/ml, 3.1±0.1 mg/ml, 3.2±0.1 mg/ml, 3.3±0.1 mg/ml, or 3.4±0.1 mg/ml. However, one of skill in the art would know how to test for stability of the anthracycline compound (e.g., DOXO-EMCH) using techniques known in the art (e.g., by HPLC).

In some embodiments, a reconstituted formulation comprises less than 2.5% free doxorubicin, for example, at room temperature. In certain embodiments, the doxorubicin has been produced via degradation of DOXO-EMCH. For example, in certain embodiments a reconstituted formulation comprises less than 2.4%, less than 2.3%, less than 2.2%, less than 2.1%, less than 2.0%, less than 1.9%, less than 1.8%, less than 1.7%, less than 1.6%, less than 1.5%, less than 1.4%, less than 1.3%, less than 1.2%, less than 1.1%, less than 1.0%, less than 0.9%, less than 0.8%, or less than 0.75% free doxorubicin at room temperature. In some embodiments, the reconstituted formulation maintains these amounts of doxorubicin (i.e., no additional doxorubicin is formed via the degradation of DOXO-EMCH present in the reconstituted formulation) at room temperature for 5, 10, 15, 20, 25, 30, 35, 40, 45, 50, 55, 60, 65, 70, 75, 80, 85, 90, 95, 100, 105, 110, 115, or 120 minutes or more after reconstitution of DOXO-EMCH. In other embodiments, the reconstituted formulation maintains these amounts of doxorubicin (i.e., no additional doxorubicin is formed via the degradation of DOXO-EMCH present in the reconstituted formulation) at room temperature for 2, 2.5, 3, 3.5, 4, 4.5, 5, 5.5, 6, 6.5, 7, 7.5, 8, 8.5, 9, 9.5, 10, 10.5, 11, 11.5, or 12 hours or more after reconstitution of DOXO-EMCH. In particular embodiments, the reconstituted formulation comprises less than 0.75% free doxorubicin at room temperature 10 minutes after reconstitution of DOXO-EMCH, e.g., when the DOXO-EMCH is reconstituted to 10 mg/ml. In particular embodiments, the reconstituted formulation comprises less than 1.1% free doxorubicin at room temperature 20 minutes after reconstitution of DOXO-EMCH, e.g., when the DOXO-EMCH is reconstituted to 10 mg/ml.

In certain embodiments, a reconstituted formulation comprises greater than 96.0% DOXO-EMCH, e.g., at room temperature. In particular embodiments, a reconstituted formulation comprises greater than 96.1%, greater than 96.2%, greater than 96.3%, greater than 96.4%, greater than 96.5%, greater than 96.6%, greater than 96.7%, greater than 96.8%, greater than 96.9%, greater than 97.0%, greater than 97.1%, greater than 97.2%, greater than 97.3%, greater than 97.4%, greater than 97.5%, greater than 97.6%, greater than 97.7%, greater than 97.8%, greater than 97.9%, greater than 98.0%, greater than 98.1%, greater than 98.2%, greater than 98.3%, greater than 98.4%, greater than 98.5%, greater than 98.6%, greater than 98.7%, greater than 98.8%, greater than 98.9%, greater than 99.0%, greater than 99.1%, greater than 99.2%, greater than 99.3%, greater than 99.4%, greater than 99.5%, greater than 99.6%, greater than 99.7%, greater than 99.8%, greater than 99.9%, or 100.0% DOXO-EMCH. In some embodiments, the reconstituted formulation maintains these amounts of DOXO-EMCH (i.e., no additional DOXO-EMCH is degraded into, e.g., free doxorubicin) at room temperature for 5, 10, 15, 20, 25, 30, 35, 40, 45, 50, 55, 60, 65, 70, 75, 80, 85, 90, 95, 100, 105, 110, 115, or 120 minutes or more after reconstitution of DOXO-EMCH. In some embodiments, the reconstituted formulation maintains these amounts of DOXO-EMCH (i.e., no additional DOXO-EMCH is degraded into, e.g., free doxorubicin) at room temperature for 2, 2.5, 3, 3.5, 4, 4.5, 5, 5.5, 6, 6.5, 7, 7.5, 8, 8.5, 9, 9.5, 10, 10.5, 11, 11.5, or 12 hours or more after reconstitution of DOXO-EMCH. In particular embodiments, the reconstituted formulation comprises greater than 99.0% DOXO-EMCH at room temperature 10 minutes after reconstitution of DOXO-EMCH, e.g., when the DOXO-EMCH is reconstituted to 10 mg/ml. In particular embodiments, the reconstituted formulation comprises greater than 96.0% DOXO-EMCH at room temperature 10 minutes after reconstitution of DOXO-EMCH, e.g., when the DOXO-EMCH is reconstituted to 10 mg/ml. In particular embodiments, the reconstituted formulation comprises 100.0% DOXO-EMCH at room temperature 10 minutes after reconstitution of DOXO-EMCH, e.g., when the DOXO-EMCH is reconstituted to 10 mg/ml. In particular embodiments, the reconstituted formulation comprises greater than 96.2% DOXO-EMCH at room temperature 20 minutes after reconstitution of DOXO-EMCH, e.g., when the DOXO-EMCH is reconstituted to 10 mg/ml. In particular embodiments, the reconstituted formulation comprises greater than 98.2% DOXO-EMCH at room temperature 20 minutes after reconstitution of DOXO-EMCH, e.g., when the DOXO-EMCH is reconstituted to 10 mg/ml.

Injectable Compositions

A reconstitution liquid comprising ethanol and water may not in itself be suitable for parenteral administration (e.g., administration by injection). Thus, there is a need for injectable compositions comprising an anthracycline compound and a reconstitution liquid. Such injectable compositions also should be suitable for an intravenous administration solution in that they are stable at room temperature, maintain the stability of the reconstituted drug product, and are easy to administer. A survey of all oncology drug products described in the Physicians' Desk Reference indicates that 5% dextrose, 0.9% NaCl, or 5% plus 0.45% NaCl are recommended for all of the intravenously administered oncology products. When tested with DOXO-EMCH, all of these solutions were associated with a rapid hydrolysis and release of free doxorubicin before the drug product could be reasonably administered to a patient at room temperature. Surprisingly, the reconstituted formulations of the invention required Lactated Ringer's solution (LR) as the administration solution to create an injectable composition suitable for administration at room temperature.

The total amount of an anthracycline compound (e.g., DOXO-EMCH) in a composition to be injected in a patient is one that is suitable for that patient. One of skill in the art would appreciate that different individuals may require different total amounts of the anthracycline compound. In some embodiments, the amount of the anthracycline compound is a pharmaceutically effective amount. The skilled worker would be able to determine the amount of the anthracycline compound in a composition needed to treat a patient based on factors such as, for example, the age, weight, and physical condition of the patient. The concentration of anthracycline compound (e.g., DOXO-EMCH) depends on its solubility in the intravenous administration solution and the volume of fluid that can be administered. For example, the concentration of the anthracycline compound may be from about 0.1 mg/ml to about 50 mg/ml in the injectable composition. In some embodiments, the concentration of the anthracycline compound may be from about 0.1 mg/ml to about 25 mg/ml, from about 7 mg/ml to about 17 mg/ml, from about 0.1 mg/ml to about 5 mg/ml, or from about 0.25 mg/ml to about 4.5 mg/ml. In particular embodiments, the concentration of anthracycline compound may be about 0.1 mg/ml, about 0.2 mg/ml, about 0.3 mg/ml, about 0.4 mg/ml, about 0.5 mg/ml, about 0.6 mg/ml, about 0.7 mg/ml, about 0.8 mg/ml, about 0.9 mg/ml, about 1.0 mg/ml, about 1.1 mg/ml, about 1.2 mg/ml, about 1.3 mg/ml, about 1.4 mg/ml, about 1.5 mg/ml, about 1.6 mg/ml, about 1.7 mg/ml, about 1.8 mg/ml, about 1.9 mg/ml, about 2.0 mg/ml, about 2.1 mg/ml, about 2.2 mg/ml, about 2.3 mg/ml, about 2.4 mg/ml, about 2.5 mg/ml, about 2.6 mg/ml, about 2.7 mg/ml, about 2.8 mg/ml, about 2.9 mg/ml, about 3.0 mg/ml, about 3.1 mg/ml, about 3.2 mg/ml, about 3.3 mg/ml, about 3.4 mg/ml, about 3.5 mg/ml, about 3.6 mg/ml, about 3.7 mg/ml, about 3.8 mg/ml, about 3.9 mg/ml, about 4.0 mg/ml, about 4.1 mg/ml, about 4.2 mg/ml, about 4.3 mg/ml, about 4.4 mg/ml, about 4.5 mg/ml, about 4.6 mg/ml, about 4.7 mg/ml, about 4.8 mg/ml, about 4.9 mg/ml, about 5.0 mg/ml, about 5.1 mg/ml, about 5.2 mg/ml, about 5.3 mg/ml, about 5.4 mg/ml, about 5.5 mg/ml, about 5.6 mg/ml, about 5.7 mg/ml, about 5.8 mg/ml, about 5.9 mg/ml, or about 6.0 mg/ml. In some embodiments, the concentration of the anthracycline compound may be about 7 mg/ml, about 8 mg/ml, about 9 mg/ml, about 10 mg/ml, about 11 mg/ml, about 12 mg/ml, about 13 mg/ml, about 14 mg/ml, about 15 mg/ml, about 16 mg/ml, about 17 mg/ml, about 18 mg/ml, about 19 mg/ml, about 20 mg/ml, about 21 mg/ml, about 22 mg/ml, about 23 mg/ml, about 24 mg/ml, about 25 mg/ml, about 26 mg/ml, about 27 mg/ml, about 28 mg/ml, about 29 mg/ml, or about 30 mg/ml.

In some embodiments, an injectable composition comprises less than 3.0% free doxorubicin, for example, at room temperature. In certain embodiments, the doxorubicin has been produced via degradation of DOXO-EMCH. For example, in certain embodiments an injectable composition comprises less than 2.9%, less than 2.8%, less than 2.7%, less than 2.6%, less than 2.5%, less than 2.4%, less than 2.3%, less than 2.2%, less than 2.1%, less than 2.0%, less than 1.9%, less than 1.8%, less than 1.7%, less than 1.6%, less than 1.5%, less than 1.4%, less than 1.3%, less than 1.2%, less than 1.1%, less than 1.0%, less than 0.9%, less than 0.8%, or less than 0.75% free doxorubicin. In some embodiments, the reconstituted formulation maintains these amounts of doxorubicin (i.e., no additional doxorubicin is formed via the degradation of DOXO-EMCH present in the reconstituted formulation) at room temperature for 5, 10, 15, 20, 25, 30, 35, 40, 45, 50, 55, 60, 65, 70, 75, 80, 85, 90, 95, 100, 105, 110, 115, or 120 minutes or more after reconstitution of DOXO-EMCH. In other embodiments, the reconstituted formulation maintains these amounts of doxorubicin (i.e., no additional doxorubicin is formed via the degradation of DOXO-EMCH present in the reconstituted formulation) at room temperature for 2, 2.5, 3, 3.5, 4, 4.5, 5, 5.5, 6, 6.5, 7, 7.5, 8, 8.5, 9, 9.5, 10, 10.5, 11, 11.5, or 12 hours or more after reconstitution of DOXO-EMCH. In particular embodiments, the injectable composition comprises less than 1.0% free doxorubicin or less than 1.1% free doxorubicin at room temperature 0 minutes after dilution, for example, in Lactated Ringer's solution and/or at a DOXO-EMCH concentration of 2.4 mg/ml. In particular embodiments, the injectable composition comprises less than 1.1% free doxorubicin or less than 1.3% free doxorubicin at room temperature 30 minutes after dilution, for example, in Lactated Ringer's solution and/or at a DOXO-EMCH concentration of 2.4 mg/ml. In particular embodiments, the injectable composition comprises less than 1.3% free doxorubicin or less than 1.5% free doxorubicin at room temperature 60 minutes after dilution, for example, in Lactated Ringer's solution and/or at a DOXO-EMCH concentration of 2.4 mg/ml. In particular embodiments, the injectable composition comprises less than 1.7% free doxorubicin at room temperature 90 minutes after dilution, for example, in Lactated Ringer's solution and/or at a DOXO-EMCH concentration of 2.4 mg/ml. In particular embodiments, the injectable composition comprises less than 1.9% free doxorubicin or less than 2.1% free doxorubicin at room temperature 120 minutes after dilution, for example, in Lactated Ringer's solution and/or at a DOXO-EMCH concentration of 2.4 mg/ml. In particular embodiments, the injectable composition comprises less than 2.3% free doxorubicin at room temperature 150 minutes after dilution, for example, in Lactated Ringer's solution and/or at a DOXO-EMCH concentration of 2.4 mg/ml. In particular embodiments, the injectable composition comprises less than 3.4% free doxorubicin at room temperature 240 minutes after dilution, for example, in Lactated Ringer's solution and/or at a DOXO-EMCH concentration of 2.4 mg/ml.

In certain embodiments, an injectable composition comprises greater than 96.0% DOXO-EMCH, e.g., at room temperature and/or at 2.4 mg/ml of DOXO-EMCH and/or when diluted in Lactated Ringer's solution. In particular embodiments, an injectable composition comprises greater than 96.1%, greater than 96.2%, greater than 96.3%, greater than 96.4%, greater than 96.5%, greater than 96.6%, greater than 96.7%, greater than 96.8%, greater than 96.9%, greater than 97.0%, greater than 97.1%, greater than 97.2%, greater than 97.3%, greater than 97.4%, greater than 97.5%, greater than 97.6%, greater than 97.7%, greater than 97.8%, greater than 97.9%, greater than 98.0%, greater than 98.1%, greater than 98.2%, greater than 98.3%, greater than 98.4%, greater than 98.5%, greater than 98.6%, greater than 98.7%, greater than 98.8%, greater than 98.9%, greater than 99.0%, greater than 99.1%, greater than 99.2%, greater than 99.3%, greater than 99.4%, greater than 99.5%, greater than 99.6%, greater than 99.7%, greater than 99.8%, greater than 99.9%, or 100.0% DOXO-EMCH. In some embodiments, the reconstituted formulation maintains these amounts of DOXO-EMCH (i.e., no additional DOXO-EMCH is degraded into, e.g., free doxorubicin) at room temperature for 5, 10, 15, 20, 25, 30, 35, 40, 45, 50, 55, 60, 65, 70, 75, 80, 85, 90, 95, 100, 105, 110, 115, or 120 minutes or more after reconstitution of DOXO-EMCH. In some embodiments, the reconstituted formulation maintains these amounts of DOXO-EMCH (i.e., no additional DOXO-EMCH is degraded into, e.g., free doxorubicin) at room temperature for 2, 2.5, 3, 3.5, 4, 4.5, 5, 5.5, 6, 6.5, 7, 7.5, 8, 8.5, 9, 9.5, 10, 10.5, 11, 11.5, or 12 hours or more after reconstitution of DOXO-EMCH.

Excipients

In some embodiments, it may be beneficial to include one or more excipients in a reconstituted formulation or an injectable composition of the invention. One of skill in the art would appreciate that the choice of any one excipient may influence the choice of any other excipient. For example, the choice of a particular excipient may preclude the use of one or more additional excipients because the combination of excipients would produce undesirable effects. One of skill in the art would be able to empirically determine which excipients, if any, to include in the formulations or compositions of the invention. Excipients of the invention may include, but are not limited to, co-solvents, solubilizing agents, buffers, pH adjusting agents, bulking agents, surfactants, encapsulating agents, tonicity-adjusting agents, stabilizing agents, protectants, and viscosity modifiers. In some embodiments, it may be beneficial to include a pharmaceutically acceptable carrier in the compositions and formulations of the invention.

Solubilizing Agents

In some embodiments, it may be beneficial to include a solubilizing agent in the formulations or compositions of the invention. Solubilizing agents may be useful for increasing the solubility of any of the components of the formulation or composition, including an anthracycline compound (e.g., DOXO-EMCH) or an excipient. The solubilizing agents described herein are not intended to constitute an exhaustive list, but are provided merely as exemplary solubilizing agents that may be used in the formulations or compositions of the invention. In certain embodiments, solubilizing agents include, but are not limited to, ethyl alcohol, tert-butyl alcohol, polyethylene glycol, glycerol, methylparaben, propylparaben, polyethylene glycol, polyvinyl pyrrolidone, and any pharmaceutically acceptable salts and/or combinations thereof.

Buffers

The pH of the reconstituted formulations and injectable compositions of the invention may be any pH that provides desirable properties for the formulation or composition. Desirable properties may include, for example, anthracycline compound (e.g., DOXO-EMCH) stability, increased anthracycline compound retention as compared to compositions at other pHs, and improved filtration efficiency. In some embodiments, the pH of the reconstituted formulations and injectable compositions of the invention may be from about 3.0 to about 9.0, e.g., from about 5.0 to about 7.0. In particular embodiments, the pH of the reconstituted formulations and injectable compositions of the invention may be 5.5±0.1, 5.6±0.1, 5.7±0.1, 5.8±0.1, 5.9±0.1, 6.0±0.1, 6.1±0.1, 6.2±0.1, 6.3±0.1, 6.4±0.1, or 6.5±0.1.

In some embodiments, it may be beneficial to buffer the pH by including one or more buffers in the compositions. In certain embodiments, a buffer may have a pKa of, for example, about 5.5, about 6.0, or about 6.5. One of skill in the art would appreciate that an appropriate buffer may be chosen for inclusion in compositions of the invention based on its pKa and other properties. Buffers are well known in the art. Accordingly, the buffers described herein are not intended to constitute an exhaustive list, but are provided merely as exemplary buffers that may be used in the formulations or compositions of the invention. In certain embodiments, a buffer includes, but is not limited to, Tris, Tris HCl, potassium phosphate, sodium phosphate, sodium citrate, sodium ascorbate, combinations of sodium and potassium phosphate, Tris/Tris HCl, sodium bicarbonate, arginine phosphate, arginine hydrochloride, histidine hydrochloride, cacodylate, succinate, 2-(N-morpholino)ethanesulfonic acid (MES), maleate, bis-tris, phosphate, carbonate, and any pharmaceutically acceptable salts and/or combinations thereof.

pH-Adjusting Agents

In some embodiments, it may be beneficial to adjust the pH of the reconstituted formulations and injectable compositions by including a pH-adjusting agent in the compositions of the invention. Modifying the pH of a formulation or composition may have beneficial effects on, for example, the stability or solubility of an anthracycline compound, or may be useful in making a formulation or composition suitable for parenteral administration. pH-adjusting agents are well known in the art. Accordingly, the pH-adjusting agents described herein are not intended to constitute an exhaustive list, but are provided merely as exemplary pH-adjusting agents that may be used in the formulations or compositions of the invention. pH-adjusting agents may include, for example, acids and bases. In some embodiments, a pH-adjusting agent includes, but is not limited to, acetic acid, hydrochloric acid, phosphoric acid, sodium hydroxide, sodium carbonate, and combinations thereof.

Bulking Agents

In some embodiments, it may be beneficial to include a bulking agent in the reconstituted formulations and injectable compositions of the invention. Bulking agents are commonly used in lyophilized compositions to provide added volume to the composition and to aid visualization of the composition, especially in instances where the lyophilized pellet would otherwise be difficult to see. Bulking agents also may help prevent a blowout of the active component(s) of a pharmaceutical composition and/or to aid cryoprotection of the composition. Bulking agents are well known in the art. Accordingly, the bulking agents described herein are not intended to constitute an exhaustive list, but are provided merely as exemplary bulking agents that may be used in the formulations or compositions of the invention.

Exemplary bulking agents may include carbohydrates, monosaccharides, disaccharides, polysaccharides, sugar alcohols, amino acids, and sugar acids, and combinations thereof. Carbohydrate bulking agents include, but are not limited to, mono-, di-, or poly-carbohydrates, starches, aldoses, ketoses, amino sugars, glyceraldehyde, arabinose, lyxose, pentose, ribose, xylose, galactose, glucose, hexose, idose, mannose, talose, heptose, glucose, fructose, methyl a-D-glucopyranoside, maltose, lactone, sorbose, erythrose, threose, arabinose, allose, altrose, gulose, idose, talose, erythrulose, ribulose, xylulose, psicose, tagatose, glucosamine, galactosamine, arabinans, fructans, fucans, galactans, galacturonans, glucans, mannans, xylans, inulin, levan, fucoidan, carrageenan, galactocarolose, pectins, amylose, pullulan, glycogen, amylopectin, cellulose, pustulan, chitin, agarose, keratin, chondroitin, dermatan, hyaluronic acid, xanthin gum, sucrose, trehalose, dextran, and lactose. Sugar alcohol bulking agents include, but are not limited to, alditols, inositols, sorbitol, and mannitol Amino acid bulking agents include, but are not limited to, glycine, histidine, and proline. Sugar acid bulking agents include, but are not limited to, aldonic acids, uronic acids, aldaric acids, gluconic acid, isoascorbic acid, ascorbic acid, glucaric acid, glucuronic acid, gluconic acid, glucaric acid, galacturonic acid, mannuronic acid, neuraminic acid, pectic acids, and alginic acid.

Surfactants

In some embodiments, it may be beneficial to include a surfactant in the reconstituted formulations and injectable compositions of the invention. Surfactants, in general, reduce the surface tension of a liquid composition. This may provide beneficial properties such as improved ease of filtration. Surfactants also may act as emulsifying agents and/or solubilizing agents. Surfactants are well known in the art. Accordingly, the surfactants described herein are not intended to constitute an exhaustive list, but are provided merely as exemplary surfactants that may be used in the formulations or compositions of the invention. Surfactants that may be included include, but are not limited to, sorbitan esters such as polysorbates (e.g., polysorbate 20 and polysorbate 80), lipopolysaccharides, polyethylene glycols (e.g., PEG 400 and PEG 3000), poloxamers (i.e., pluronics), ethylene oxides and polyethylene oxides (e.g., Triton X-100), saponins, phospholipids (e.g., lecithin), and combinations thereof.

Encapsulating Agents

In some embodiments, it may be beneficial to include an encapsulating agent in the reconstituted formulations and injectable compositions of the invention. Encapsulating agents can sequester molecules and help stabilize or solubilize them. Encapsulating agents are well known in the art. Accordingly, the encapsulating agents described herein are not intended to constitute an exhaustive list, but are provided merely as exemplary encapsulating agents that may be used in the formulations or compositions of the invention. Encapsulating agents that may be included in compositions include, but are not limited to, dimethyl-β-cyclodextrin, hydroxyethyl-β-cyclodextrin, hydroxypropyl-β-cyclodextrin, and trimethyl-β-cyclodextrin, and combinations thereof.

Tonicity-Adjusting Agents

In some embodiments, it may be beneficial to include a tonicity-adjusting agent in the reconstituted formulations and injectable compositions of the invention. The tonicity of a liquid composition is an important consideration when administering the composition to a patient, for example, by parenteral administration. Tonicity-adjusting agents, thus, may be used to help make a formulation or composition suitable for administration. Tonicity-adjusting agents are well known in the art. Accordingly, the tonicity-adjusting agents described herein are not intended to constitute an exhaustive list, but are provided merely as exemplary tonicity-adjusting agents that may be used in the formulations or compositions of the invention. Tonicity-adjusting agents may be ionic or non-ionic and include, but are not limited to, inorganic salts, amino acids, carbohydrates, sugars, sugar alcohols, and carbohydrates. Exemplary inorganic salts may include sodium chloride, potassium chloride, sodium sulfate, and potassium sulfate. An exemplary amino acid is glycine. Exemplary sugars may include sugar alcohols such as glycerol, propylene glycol, glucose, sucrose, lactose, and mannitol.

Stabilizing Agents

In some embodiments, it may be beneficial to include a stabilizing agent in the reconstituted formulations and injectable compositions of the invention. Stabilizing agents help increase the stability of an anthracycline compound in compositions of the invention. This may occur by, for example, reducing degradation or preventing aggregation of an anthracycline compound. Without wishing to be bound by theory, mechanisms for enhancing stability may include sequestration of the anthracycline compound from a solvent or inhibiting free radical oxidation of the anthracycline compound. Stabilizing agents are well known in the art. Accordingly, the stabilizing agents described herein are not intended to constitute an exhaustive list, but are provided merely as exemplary stabilizing agents that may be used in the formulations or compositions of the invention. Stabilizing agents may include, but are not limited to, emulsifiers and surfactants.

Protectants

In some embodiments, it may be beneficial to include a protectant in the reconstituted formulations and injectable compositions of the invention. Protectants are agents that protect a pharmaceutically active ingredient (e.g., an anthracycline compound) from an undesirable condition (e.g., instability caused by freezing or lyophilization, or oxidation). Protectants can include, for example, cryoprotectants, lyoprotectants, and antioxidants. Cryoprotectants are useful in preventing loss of potency of an active pharmaceutical ingredient (e.g., an anthracycline compound) when a formulation is exposed to a temperature below its freezing point. For example, a cryoprotectant could be included in a reconstituted lyophilized formulation of the invention so that the formulation could be frozen before dilution for intravenous (IV) administration. Cryoprotectants are well known in the art. Accordingly, the cryoprotectants described herein are not intended to constitute an exhaustive list, but are provided merely as exemplary cryoprotectants that may be used in the formulations or compositions of the invention. Cryoprotectants include, but are not limited to, solvents, surfactants, encapsulating agents, stabilizing agents, viscosity modifiers, and combinations thereof. Cryoprotectants may include, for example, disaccharides (e.g., sucrose, lactose, maltose, and trehalose), polyols (e.g., glycerol, mannitol, sorbitol, and dulcitol), glycols (e.g., ethylene glycol, polyethylene glycol, propylene glycol).

Lyoprotectants are useful in stabilizing the components of a lyophilized formulation or composition. For example, an anthracycline compound could be lyophilized with a lyoprotectant prior to reconstitution. Lyoprotectants are well known in the art. Accordingly, the lyoprotectants described herein are not intended to constitute an exhaustive list, but are provided merely as exemplary lyoprotectants that may be used in the formulations or compositions of the invention. Lyoprotectacts include, but are not limited to, solvents, surfactants, encapsulating agents, stabilizing agents, viscosity modifiers, and combinations thereof. Exemplary lyoprotectants may be, for example, sugars and polyols. Trehalose, sucrose, dextran, and hydroxypropyl-beta-cyclodextrin are non-limiting examples of lyoprotectants.

Antioxidants are useful in preventing oxidation of the components of a formulation or composition. Oxidation may result in aggregation of a drug product or other detrimental effects to the purity of the drug product or its potency. Antioxidants are well known in the art. Accordingly, the antioxidants described herein are not intended to constitute an exhaustive list, but are provided merely as exemplary antioxidants that may be used in the formulations or compositions of the invention. Antioxidants may be, for example, sodium ascorbate, citrate, thiols, metabisulfite, and combinations thereof.

Viscosity Modifiers

In some embodiments, it may be beneficial to include a viscosity modifying agent in the reconstituted formulations and injectable compositions of the invention. Viscosity modifiers change the viscosity of liquid formulations or compositions of the invention. This may be beneficial because viscosity plays an important role in the ease with which a liquid composition is filtered. A reconstituted formulation of the invention may be filtered prior to lyophilization and reconstitution, or after reconstitution. Viscosity modifiers are well known in the art. Accordingly, the viscosity modifiers described herein are not intended to constitute an exhaustive list, but are provided merely as exemplary viscosity modifiers that may be used in the formulations or compositions of the invention. Viscosity modifiers include solvents, solubilizing agents, surfactants, and encapsulating agents. Exemplary viscosity modifiers that may be included in compositions include, but are not limited to, N-acetyl-DL-tryptophan and N-acetyl-cysteine.

Treatment of Diseases and/or Conditions

The reconstituted formulations and injectable compositions provided herein are useful for a variety of clinical applications. Anthracyclines are useful in the treatment of cancer. For example, doxorubicin is an intercalating agent as well as a topoisomerase II inhibitor, and preferentially kills rapidly dividing cells, such as tumor cells. DOXO-EMCH is an anthracycline compound that can be used to treat solid tumors as well as hematological malignancies. DOXO-EMCH acts by covalently binding to albumin wherein the free thiol of cysteine-34 of albumin binds the DOXO-EMCH maleimide via a Michael attack. It is believed that DOXO-EMCH-albumin conjugate then circulates in the bloodstream until reaching a tumor, where the lower pH in the tumor results in cleavage of the hydrazone bond between doxorubicin and the EMCH moiety, thereby releasing the doxorubicin.

The reconstituted formulations and injectable compositions of the invention may be administered for the treatment of various diseases or conditions, or used in the manufacture of a medicament for the treatment of various diseases or conditions. Exemplary cancers that may be treated include the following non-limiting examples: a solid tumor cancer, breast cancer, lung cancer, endometrial cancer, ovarian cancer, pancreatic cancer, cancer of the adrenal cortex, non-Hodgkin's lymphoma, multiple myeloma, leukemia, Kaposi's sarcoma, Ewing's sarcoma, soft tissue sarcoma, nephroblastoma, glioblastoma, prostate cancer, liver cancer, bone cancer, chondrosarcoma, renal cancer, bladder cancer, and gastric cancer. In certain embodiments, the cancer is selected from: a solid tumor cancer and a soft tissue sarcoma. In particular embodiments, the pancreatic cancer is pancreatic ductal adenocarcinoma.

Administration of Injectable Compositions

As described herein, the injectable compositions of the invention are suitable for parenteral administration. These compositions may be administered, for example, intraperitoneally, intravenously, or intrathecally. One of skill in the art would appreciate that a method of administering an anthracycline compound formulation or composition of the invention would depend on factors such as the age, weight, and physical condition of the patient being treated, and the disease or condition being treated. The skilled worker would, thus, be able to select a method of administration optimal for a patient on a case-by-case basis.

Preparation and Uses of Anthracycline Compound Formulations

In some embodiments, a reconstituted formulation or injectable composition of the present invention may be used in the manufacture of a medicament for treating cancer. In some embodiments, a reconstituted formulation of the invention can be prepared by reconstituting a lyophilized anthracycline compound composition in a reconstitution liquid comprising ethanol and water. Such reconstitution may comprise adding the reconstitution liquid and mixing, for example, by swirling or vortexing the mixture. The reconstituted formulation then can be made suitable for injection by mixing Lactated Ringer's solution with the formulation to create an injectable composition.

Stability of Anthracycline Compound Compositions

An important factor of the reconstituted formulations and injectable compositions of the invention is the stability of the anthracycline compound present in the compositions. For example, degradation of DOXO-EMCH into doxorubicin and EMCH is known to occur in solution. Thus, it is important to test for stability of an anthracycline compound of the invention, for example, by HPLC. Stability can be measured by measuring the quantity of the anthracycline compound (e.g., DOXO-EMCH) or a degradation product thereof (e.g., doxorubicin) in a sample at two or more time points, and comparing the quantities. Presence of a parent anthracycline (e.g., doxorubicin) from which an anthracycline compound of the invention (e.g., DOXO-EMCH) has been derived is indicative of instability of the anthracycline compound of the invention. Likewise, aggregation of the anthracycline compound also is indicative of instability. In some embodiments, a composition is stable when the quantity of the undegraded anthracycline compound at a second time point is about 60%, about 65%, about 70%, about 75%, about 80%, about 85%, about 90%, about 91%, about 92%, about 93%, about 94%, about 95%, about 96%, about 97%, about 98%, about 99%, or about 100% of the quantity of the undegraded anthracycline compound at the first time point. In some embodiments, a composition is stable when the quantity of the undegraded anthracycline compound at a second time point is at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or at least about 100% of the quantity of the undegraded anthracycline compound at the first time point.

In some embodiments, a reconstituted formulation or injectable composition is stable when stored at a temperature from about −80° C. to about 30° C., for example when stored at a temperature from about −80° C. to about −70° C., from about −25° C. to about −15° C., from about 0° C. to about 10° C., from about 2° C. to about 8° C., from about 15° C. to about 30° C., or from about 20° C. to about 30° C. Exemplary temperatures include, but are not limited to, −85.0±1.0° C., −84.0±1.0° C., −83.0±1.0° C., −82.0±1.0° C., −81.0±1.0° C., −80.0±1.0° C., −79.0±1.0° C., −78.0±1.0° C., −77.0±1.0° C., −76.0±1.0° C., −75.0±1.0° C., −74.0±1.0° C., −73.0±1.0° C., −72.0±1.0° C., −71.0±1.0° C., −70.0±1.0° C., −69.0±1.0° C., −68.0±1.0° C., −67.0±1.0° C., −66.0±1.0° C., and −65.0±1.0° C. Further exemplary temperatures include −25.0±1.0° C., −24.0±1.0° C., −23.0±1.0° C., −22.0±1.0° C., −21.0±1.0° C., −20.0±1.0° C., −19.0±1.0° C., −18.0±1.0° C., −17.0±1.0° C., −16.0±1.0° C., and −15.0±1.0° C. Still further exemplary temperatures include 0.0±1.0° C., 0.5±1.0° C., 1.0±1.0° C., 1.5±1.0° C., 2.0±1.0° C., 2.5±1.0° C., 3.0±1.0° C., 3.5±1.0° C., 4.0±1.0° C., 4.5±1.0° C., 5.0±1.0° C., 5.5±1.0° C., 6.0±1.0° C., 6.5±1.0° C., 7.0±1.0° C., 7.5±1.0° C., and 8.0±1.0° C. Additional exemplary temperatures include 20.0±1.0° C., 21.0±1.0° C., 22.0±1.0° C., 23.0±1.0° C., 24.0±1.0° C., 25.0±1.0° C., 26.0±1.0° C., 27.0±1.0° C., 28.0±1.0° C., 29.0±1.0° C., and 30.0±1.0° C.

In some embodiments, a reconstituted formulation or injectable composition is stable when stored at a temperature from about −80° C. to about 30° C., for example from about −80° C. to about 0° C., from about −80° C. to about −10° C., or from about −30° C. to about −10° C. Exemplary temperatures include, but are not limited to, −30.0±1.0° C., −29.0±1.0° C., 28.0±1.0° C., −27.0±1.0° C., −26.0±1.0° C., −25.0±1.0° C., −24.0±1.0° C., −23.0±1.0° C., −22.0±1.0° C., −21.0±1.0° C., −20.0±1.0° C., −19.0±1.0° C., −18.0±1.0° C., −17.0±1.0° C., −16.0±1.0° C., −15.0±1.0° C., −14.0±1.0° C., −13.0±1.0° C., −12.0±1.0° C., −11.0±1.0° C., and −10.0±1.0° C. In some embodiments, a reconstituted formulation or injectable composition is stable when stored at a temperature from about −5° C. to about 10° C., or from about 2° C. to about 8° C. Exemplary temperatures include, but are not limited to, 2.0±1.0° C., 3.0±1.0° C., 4.0±1.0° C., 5.0±1.0° C., 6.0±1.0° C., 7.0±1.0° C., and 8.0±1.0° C. In some embodiments, a reconstituted formulation or injectable composition is stable when stored at a temperature from about 10° C. to about 35° C., for example when stored at a temperature from about 15° C. to about 30° C., from about 18° C. to about 30° C., or from about 20° C. to about 30° C. Exemplary temperatures include, but are not limited to, about 18° C., about 19° C., about 20° C., about 21° C., about 22° C., about 23° C., about 24° C., about 25° C., about 26° C., about 27° C., about 28° C., about 29° C., and about 30° C.

One of skill in the art would know how to test for stability of the anthracycline compound (e.g., DOXO-EMCH) using techniques known in the art (e.g., by HPLC).

Variations and Modifications

Variations, modifications, and other implementations of what is described herein will occur to those of ordinary skill without departing from the spirit and the scope of the invention. Accordingly, the invention is not to be limited only to the preceding illustrative description. For additional illustrative features that may be used with the invention, including the embodiments described here, refer to the documents listed herein (e.g., U.S. Pat. Nos. 7,387,771 and 7,902,144 and U.S. patent application Ser. No. 12/619,161), each of which is incorporated by reference in its entirety.

Each of the embodiments of the invention may be combined individually or in combination with one or more other embodiments of the invention.

EXEMPLIFICATION

With aspects of the invention now being generally described, these will be more readily understood by reference to the following examples, which are included merely for purposes of illustration of certain features and embodiments of the invention and are not intended to be limiting.

EQUIVALENTS

Those skilled in the art will recognize, or be able to ascertain using no more than routine experimentation, numerous equivalents to the compounds, compositions, and methods of use thereof described herein. Such equivalents are considered to be within the scope of the invention.

The contents of all references, patents and published patent applications cited throughout this Application, as well as their associated figures are hereby incorporated by reference in their entirety.

EXAMPLES

Analytical Methodology

To analyze DOXO-EMCH's behavior in solution, a reversed-phase (RP) HPLC method for quantitation of DOXO-EMCH and various impurities and degradation products was utilized. Samples (1.0 µL injection volume) were assayed on an HPLC system fitted with a Phenomenex Gemini C18 column 100×2.0 mm, 3 µm at a flow rate of 0.3 mL/min. The mobile phase used was an acetate/acetonitrile gradient. The degradation product EMCH could not be detected using the above HPLC method, and was therefore determined using a liquid chromatography-mass spectrometry (LC-MS) method.

Example 1

Studies were performed to examine the effects of pH on DOXO-EMCH stability. In these studies, a criterion of less than 3% doxorubicin over 3-5 hours was set as the goal for stability of DOXO-EMCH. Overall, studies were designed to measure the degradation of DOXO-EMCH at room temperature into doxorubicin and EMCH. Doxorubicin was measured as a percentage of the starting DOXO-EMCH material. Tables 4-6 list the results for the pH stability study. Due to solubility issues, the buffer controlled pH portion of the study could not be completed at pH 5.0, 5.5, 6.0 and 7.0. The results below are for DOXO-EMCH dissolved in DI Water at low (2.0 mg/mL) and high (20.0 mg/mL) concentration, and DOXO-EMCH dissolved in pH 4.0 phosphate citrate buffer at low concentration. In summary, none of the conditions met the goal of less than 3% doxorubicin HCl over a 3-5 hour period. The low concentration DOXO-EMCH was more stable than the high concentration DOXO-EMCH in DI Water (Table 4 and Table 5). The DOXO-EMCH dissolved in pH 4.0 phosphate citrate buffer was very unstable, likely as a result of the breakdown of the molecule at pH values below ~4.5 (Table 6).

TABLE 4

Low concentration (~2.0 mg/mL) results, no pH adjustment

| Sample time point (hr) | pH | DOXO-EMCH wt % | Doxorubicin wt % |
|---|---|---|---|
| 0 | 6.0 | 95.8 | 0.6 |
| 2 | 5.4 | 82.8 | 3.7 |
| 4 | 5.1 | 76.7 | 8.9 |
| 6 | 5.0 | 68.6 | 14.3 |

TABLE 5

High concentration (~20.0 mg/mL) results, no pH adjustment

| Sample time point (hr) | pH | DOXO-EMCH wt % | Doxorubicin wt % |
|---|---|---|---|
| 0 | 4.8 | 86.0 | 7.8 |
| 2 | 4.6 | 74.9 | 15.6 |
| 4 | 4.5 | 56.7 | 24.8 |
| 6 | 4.6 | 45.2 | 32.2 |

TABLE 6

Low concentration (~2.0 mg/mL) in pH 4.0 phosphate citrate buffer

| Sample time point (hr) | pH | DOXO-EMCH wt % | Doxorubicin wt % |
|---|---|---|---|
| 0 | 4.0 | 65.1 | 23.5 |
| 2 | 4.0 | 7.3 | 66.1 |
| 4 | 4.0 | 2.9 | 68.8 |
| 6 | N/D* | N/D* | N/A |

*Measurements not taken at 6 hr because DOXO-EMCH was approximately 97% degraded at 4 hr An additional study was performed to obtain data on the stability of DOXO-EMCH dissolved in DI water with manual pH adjustment. The initial pH of the DOXO-EMCH solution (~2.0 mg/mL) dissolved in DI Water was 5.4. At 30 minute intervals, the pH of the DOXO-EMCH solution was checked and adjusted to pH ~6.1 by the dropwise addition of a 0.1 N NaOH solution. Although the results did not meet the goal of less than 3% Doxorubicin over 3-5 hours (Table 7), the doxorubicin Wt % was lower over the 6-hour period than in the study with no pH adjustment.

TABLE 7

Manual pH adjustment

| Sample time point (hr) | DOXO-EMCH wt % | Doxorubicin wt % |
|---|---|---|
| 0 | 98.8 | 0.5 |
| 2 | 91.8 | 2.4 |
| 4 | 85.6 | 3.6 |
| 6 | 80.6 | 4.3 |

Example 2

To obtain baseline data on the stability of DOXO-EMCH at the point of use, a study was designed to determine degradation of DOXO-EMCH when combined with candidate intravenous (IV) bag solutions. IV bag solutions including Dextrose 5% in Water (D5W), Lactated Ringers (LR), and Sodium Chloride Solution 0.9% (Normal Saline; NS) were used. 100 mg of DOXO-EMCH active pharmaceutical ingredient (API) were dissolved in 50 mL of the IV bag solution for a concentration of ~2 mg/mL DOXO-EMCH API. The IV bag solutions containing API were then aliquoted in glass vials. The vials were stored at 25° C. in a stability chamber for the length of the experiment. Prior to the beginning of the IV bag stability study, all IV bag solutions were tested for pH and the presence of any peaks interfering with DOXO-EMCH or any degradation peaks of interest. Samples were pulled at 0 hr, 2 hr, 4 hr, and 6 hr time intervals and tested for pH and in duplicate by HPLC.

Tables 8-10 below list the results for the IV bag study using 0.9% NaCl, D5W, and Lactated Ringer's Solution. In summary, the 0.9% NaCl and Lactated Ringer's solutions met the goal of less than 3% doxorubicin over 3-5 hours. However, the DOXO-EMCH was not completely soluble in 0.9% NaCl or Lactated Ringer's. The sample was opaque and precipitated material visibly settled over a 2-hour period. By contrast, DOXO-EMCH was completely soluble in ethanol:water and, surprisingly, went into solution quickly (e.g., within less than a minute). The samples were mixed well before dilution of each sample for HPLC assay, but non-homogeneity of these samples is reflected in the DOXO-EMCH recovery values for those two IV bag solutions. The D5W solution formed a clear red solution showing that DOXO-EMCH was completely soluble in D5W, but also had significant degradation of DOXO-EMCH and formation of doxorubicin over a 6 hour period (Table 9). The pH for D5W was the lowest of all the IV bag solutions tested.

TABLE 8

0.9% NaCl IV solution

| Sample time point (hr) | pH | Doxorubicin (wt %) |
|---|---|---|
| 0 | 6.5 | 0.3 |
| 2 | 6.0 | 0.9 |
| 4 | 5.6 | 2.1 |
| 6 | 5.7 | 2.6 |

TABLE 9

D5W IV solution

| Sample time point (hr) | pH | Doxorubicin (wt %) |
|---|---|---|
| 0 | 5.5 | 1.6 |
| 2 | 5.0 | 5.8 |
| 4 | 4.9 | 11.2 |
| 6 | 4.8 | 16.8 |

TABLE 10

LR IV solution

| Sample time point (hr) | pH | Doxorubicin (wt %) |
|---|---|---|
| 0 | 6.3 | 0.2 |
| 2 | 6.1 | 0.5 |
| 4 | 6.0 | 0.9 |
| 6 | 5.9 | 1.6 |

Example 3

Having established preliminary information on DOXO-EMCH's properties when dissolved in NS, LR, and D5W, a follow-up study was designed to evaluate (1) the solubility and stability of DOXO-EMCH in selected diluents upon reconstitution and (2) the subsequent stability of various IV Admixtures. Diluents included Sterile Water for Injection (SWFI), Lactated Ringers Solution (LR), and 50% (v/v) ethanol/SWFI. This study was conducted in two parts: the first part to determine if lyophilized DOXO-EMCH was completely soluble in at least one of the above diluents at 10 mg/mL and stable for up to 20 minutes; and the second part to determine the stability of a LR admixture at a final DOXO-EMCH concentration of approximately 2.4 mg/mL.

The study evaluating solubility and stability of lyophilized DOXO-EMCH reconstituted in SWFI, LR, and 50% (v/v) ethanol/SWFI was conducted using a target DOXO-EMCH concentration of 10 mg/mL. To obtain a 10 mg/mL concentration, 20 mL of diluent was added to a vial containing 200 mg of lyophilized DOXO-EMCH, and the vial was gently swirled to dissolve the contents and obtain a homogeneous mixture. The sample was mixed and visually inspected for complete reconstitution to a clear solution for a) approximately 30 seconds, b) approximately 60 seconds, and c) 120 seconds, then up to a total of 10 minutes. If more than 120 seconds were required for visual clarity, the vial may have been intermittently swirled up to a maximum of 10 minutes. Duplicate vials were prepared for each study. Each vial was assessed 10 minutes and 20 minutes after the addition of reconstitution diluent for visual appearance of the reconstituted solution and sampled at these time points for determination of DOXO-EMCH content, doxorubicin content, and solution pH. If a given diluent was determined to provide acceptable solubilization and stability of the vial contents after 20 minutes at ambient conditions, the diluent proceeded directly to part 2 of the study.

IV Admixture stability studies were designed to use the reconstitution diluent found suitable in part 1 following the procedure outlined below. Briefly, to prepare an IV Admixture solution containing approximately 2.4 mg/mL DOXO-EMCH, the required volume for reconstitution was withdrawn from the IV infusion solution bag intended for final administration. The required volume for reconstitution of the respective diluent was measured and transferred into a vial of lyophilized DOXO-EMCH. The vial of DOXO-EMCH and diluent was gently swirled to dissolve the vial contents and obtain a homogeneous mixture. The reconstituted solution of drug product was inspected to ensure that the drug was completely dissolved and that no foreign matter was present. This procedure was repeated for the total number of vials required to prepare the calculated dose of DOXO-EMCH in IV infusion solution. The required volume of reconstituted DOXO-EMCH solution was then withdrawn from the drug product vials using a suitably sized syringe, and injected into the IV infution solution bag. The contents of the IV infusion solution bag were thoroughly mixed to obtain a homogeneous mixture. The IV infusion bag was then stored at room temperature and protected from light.

The IV Admixture study was performed by first removing 3 vials of 200 mg lyophilized DOXO-EMCH drug product from storage at −20° C. and allowing the vials to come to room temperature. Next, the volume required for reconstitution of three vials of DOXO-EMCH drug product (60 mL for a 10 mg/mL reconstituted drug product) was withdrawn from the infusion solution bag to be used for preparing the IV Admixture using a syringe. Each of the vials was reconstituted as described above. The required volume of the reconstitution diluent (20 mL) was drawn into an appropriate plastic syringe using a needle and injected through the stopper of each vial. The reconstituted vial was then swirled and visually inspected for complete reconstitution to form a clear, homogeneous solution. The time required to form a clear, homogeneous solution was recorded. The required volume (20.0 mL of a 10 mg/mL constituted solution) was transferred from each reconstituted vial into the 250 mL IV Admixture solution as described above. Briefly, the required volume (20.0 mL of a 10 mg/mL constituted solution) was withdrawn using an appropriate plastic syringe and needle, the required volume of constituted drug product was transferred from each of three vials into the 250 mL IV Admixture using an appropriate plastic syringe and needle, and the contents of the IV Admixture were completely mixed to obtain a homogeneous mixture at a target concentration of approximately 2.4 mg/mL. The IV bag was weighed prior to injection of constituted drug product. The contents of the IV Admixture infusion bag were then analyzed at 0, 60, and 120, 150, and 240 minutes by removing 10.0 mL of the solution, diluting with chilled HPLC method diluent to achieve a target concentration of 0.24 mg/mL, and injecting into the HPLC. Duplicate injections were made for each time point. The pH of the IV Admixture and sample prepared for HPLC analysis were also measured at each time point. The empty IV bag was weighed at study completion to calculate the actual IV Admixture solution volume in each bag.

The reconstituted solution was evaluated for color, clarity, and absence of insoluble material in the vial after every 30 seconds of mixing. Following addition of the reconstituted drug product solution to the IV bag, the resulting IV Admixture was evaluated for color, clarity, and absence of any insoluble material immediately after mixing and at each analytical time point. The amount (area %) of the degradation product doxorubicin was determined at each time point.

DOXO-EMCH was first tested for reconstitution in SWFI. Solutions appeared visually clear after mixing with SWFI for 90-120 seconds, although a few undissolved particles remained in the vial. Table 11 depicts the results of the study, which demonstrated average doxorubicin percentages of 1.54% and 1.27% for the two trials, respectively, at 20 minutes. By contrast, the average amount of doxorubicin at 20 minutes was lower (0.97% and 0.95% for two trials) when DOXO-EMCH was reconstituted in LR (Table 12). The solutions also appeared visually clear after mixing for 120 seconds. In both SWFI and LR, a peak slowly formed at RRT 1.02 (not shown); this peak has been shown to contain dimeric forms of DOXO-EMCH. Finally, a study was performed testing reconstitution of DOXO-EMCH in 50:50 ethanol:water (Table 13). The average amount of doxorubicin at 20 minutes (1.03% and 1.05% for the two trials) was similar to that seen for drug product reconstituted in LR, and the solutions appeared visually clear after mixing for 120 seconds.

TABLE 11

Stability of DOXO-EMCH lyophilized drug product reconstituted in SWFI

| | 10 minutes | | | 20 minutes | | |
|---|---|---|---|---|---|---|
| Sample | DOXO-EMCH Recovery* | Doxorubicin (Area %) | pH | DOXO-EMCH Recovery* | Doxorubicin (Area %) | pH |
| Sample 1 Injection 1 | 103% | 1.35% | | 101.4% | 1.52% | |
| Sample 1 Injection 2 | 98.6% | 1.37% | | 95.5% | 1.56% | |
| Sample 1 Average | 100.8% | 1.36% | 5.3 | 98.5% | 1.54% | 5.5 |
| Sample 2 Injection 1 | 100% | 1.06% | | 100.1% | 1.29% | |
| Sample 2 Injection 2 | 96% | 1.14% | | 95.3% | 1.26% | |
| Sample 2 Average | 98% | 1.1% | 5.4 | 97.8% | 1.27% | 5.1 |

*DOXO-EMCH HPLC recovery based on the cake weights.

TABLE 12

Stability of DOXO-EMCH lyophilized drug product reconstituted in LR

| | 10 minutes | | | 20 minutes | | |
|---|---|---|---|---|---|---|
| | DOXO-EMCH Recovery* | Doxorubicin (Area %) | pH | DOXO-EMCH Recovery* | Doxorubicin (Area %) | pH |
| Sample 1 Injection 1 | 103.8 | 0.97 | | 101.8 | 0.99 | |
| Sample 1 Injection 2 | 100.3 | 1.00 | | 98.5 | 0.95 | |
| Sample 1 Average | 102.1 | 0.99 | 5.9 | 100.1 | 0.97 | 5.8 |
| Sample 2 Injection 1 | 103.4 | 0.90 | | 98.4 | 0.94 | |
| Sample 2 Injection 2 | 101.3 | 0.97 | | 97.5 | 0.96 | |
| Sample 2 Average | 102.3 | 0.94 | 6.0 | 98 | 0.95 | 5.9 |

*DOXO-EMCH HPLC recovery based on the cake weights.

TABLE 13

Stability of DOXO-EMCH lyophilized drug product reconstituted in 50:50 ethanol:water

| Sample | 10 minutes | | | 20 minutes | | |
|---|---|---|---|---|---|---|
| | DOXO-EMCH Recovery* | Doxorubicin (Area %) | pH | DOXO-EMCH Recovery | Doxorubicin (Area %) | pH |
| Sample 1 Injection 1 | 99.1% | 0.71 | | 96.36% | 1.02 | |
| Sample 1 Injection 2 | 96.3% | 0.71 | | 96.55% | 1.03 | |
| Sample 1 Average | 97.7% | 0.71% | 5.9 | 96.5% | 1.03% | 5.7 |
| Sample 2 Injection 1 | 101.6% | 0.73 | | 98.73 | 1.01 | |
| Sample 2 Injection 2 | 102.1% | 0.72 | | 98.31 | 1.08 | |
| Sample 2 Average | 101.9% | 0.73% | 5.9 | 98.5% | 1.05% | 5.8 |

*DOXO-EMCH HPLC recovery based on the cake weights.

Next, DOXO-EMCH was tested for stability in LR after reconstitution in SWFI, LR, or 50:50 ethanol/water. Briefly, lyophilized DOXO-EMCH was reconstituted with each of the above diluents at a concentration of approximately 10 mg/mL, then further diluted in a 250 mL LR IV bag to a final concentration of approximately 2.4 mg/mL. The IV bag was maintained under ambient temperature for the duration of the study and sampled at the indicated time points. Degradation of DOXO-EMCH (measured by doxorubicin content of the solution) and pH were determined for each sample. Results for DOXO-EMCH drug product reconstituted in SWFI and diluted in LR are shown in Table 14. The doxorubicin content was about 2.3% at the two hour time point. The pH dropped by about 0.4 units (from about 6.1 to about 5.7) from zero to two hours.

TABLE 14

Degradation (as measured by doxorubicin content) of DOXO-EMCH lyophilized drug product reconstituted in SWFI and diluted in LR

| Time Point (min.) | Doxorubicin Area % | pH |
|---|---|---|
| 0 | 1.23 | 6.14 |
| 30 | 1.40 | 5.98 |
| 60 | 1.88 | 5.84 |
| 120 | 2.34 | 5.74 |
| 150 | 3.23 | 5.73 |
| 240 | 4.23 | 5.62 |

The results for two studies using DOXO-EMCH drug product reconstituted in LR and diluted in LR are depicted in Tables 15 and 16. The average doxorubicin content was about 2.4% at the two hour time point. From zero to two hours, the pH dropped by 0.2-0.3 units in the two studies.

TABLE 15

Degradation (as measured by doxorubicin content) of DOXO-EMCH lyophilized drug product reconstituted in LR and diluted in LR (Study #1)

| Time Point (min.) | Doxorubicin Area % | pH |
|---|---|---|
| 0 | 1.10 | 5.99 |
| 30 | 1.28 | 5.87 |
| 60 | 1.74 | 5.85 |
| 120 | 2.24 | 5.76 |
| 150 | 2.93 | 5.75 |
| 240 | 3.80 | 5.67 |

TABLE 16

Degradation (as measured by doxorubicin content) of DOXO-EMCH reconstituted in LR and diluted in LR (Study #2)

| Time Point (min.) | Doxorubicin Area % | pH |
|---|---|---|
| 0 | 1.03 | 6.10 |
| 30 | 1.04 | 5.98 |
| 60 | 1.68 | 5.94 |
| 90 | 1.67 | 5.89 |
| 120 | 2.53 | 5.79 |
| 150 | 2.50 | 5.77 |

The results for two studies using DOXO-EMCH drug product reconstituted in 50:50 ethanol:water and diluted in LR are depicted in Tables 17 and 18. The average doxorubicin content was 2.0% at the two hour time point. From zero to two hours, the pH dropped by 0.3-0.4 units in the two studies. Unexpectedly, the pH at this timepoint was higher (average of 5.9) than in the SWFI and LR-reconstituted IV solutions (5.7 and average of 5.8, respectively).

TABLE 17

Degradation (as measured by doxorubicin content) of DOXO-EMCH lyophilized drug product reconstituted in ethanol:water and diluted in LR (Study #1)

| Time Point (min.) | Doxorubicin Area % | pH |
|---|---|---|
| 0 | 1.0 | 6.22 |
| 30 | 1.1 | 6.04 |
| 60 | 1.3 | 5.95 |
| 90 | 1.7 | 5.89 |
| 120 | 1.9 | 5.83 |
| 150 | 2.3 | 5.82 |

TABLE 18

Degradation (as measured by doxorubicin content) of DOXO-EMCH lyophilized drug product reconstituted in ethanol:water and diluted in LR (Study #2)

| Time Point (min.) | Doxorubicin Area % | pH |
|---|---|---|
| 0 | 1.1 | 6.19 |
| 30 | 1.3 | 6.05 |
| 60 | 1.5 | 5.99 |
| 120 | 2.1 | 5.89 |
| 150 | 2.3 | 5.87 |
| 240 | 3.4 | 5.80 |

In summary, IV solutions of DOXO-EMCH in LR prepared with lyophilized DOXO-EMCH drug product reconstituted in any of the three diluents (SWFI, LR, and 50:50 ethanol/water) were relatively stable for two hours or more, based on the accumulation of the doxorubicin degradation product in the test solutions. The IV solution prepared using ethanol/water as reconstitution diluent showed less degradation (2.0% doxorubicin) at two hours than the solutions prepared using the other reconstitution diluents (2.3% and 2.4% doxorubicin respectively for SWFI and LR). Since the primary degradation pathway for DOXO-EMCH is cleavage of the acid-labile linker at low pH, the higher pH afforded by use of the ethanol/water diluent may explain its superior performance.

What is claimed is:

1. A reconstituted formulation comprising:
an anthracycline compound;
a reconstitution liquid; and
an agent selected from the group consisting of a bulking agent, a cryoprotectant, and a lyoprotectant,
wherein said reconstituted formulation is prepared by reconstituting a lyophilized composition of the anthracycline compound in a reconstitution liquid comprising ethanol and water,
wherein said reconstituted formulation is a solution, and wherein the anthracycline compound is DOXO-EMCH.

2. The reconstituted formulation of claim 1, wherein the volume:volume ratio of ethanol:water is selected from the group consisting of about 10:90 to about 90:10.

3. The reconstituted formulation of claim 2, wherein the volume:volume ratio of ethanol:water is about 40:60 to about 60:40.

4. The reconstituted formulation of claim 3, wherein the volume:volume ratio of ethanol:water is about 45:55 to about 55:45.

5. The reconstituted formulation of claim 4, wherein the volume:volume ratio of ethanol:water is about 50:50.

6. The reconstituted formulation of claim 1, wherein the concentration of the anthracycline compound in the reconstituted formulation is from about 1 mg/ml to about 30 mg/ml.

7. The reconstituted formulation of claim 6, wherein the concentration of the anthracycline compound in the reconstituted formulation is from about 5 mg/ml to about 25 mg/ml.

8. The reconstituted formulation of claim 7, wherein the concentration of the anthracycline compound in the reconstituted formulation is about 10 mg/ml.

9. The reconstituted formulation of claim 1, wherein the agent is a bulking agent.

10. The reconstituted formulation of claim 1, wherein the agent is a cryoprotectant.

11. The reconstituted formulation of claim 1, wherein the agent is a lyoprotectant.

12. An injectable composition of an anthracycline compound comprising the reconstituted formulation of claim 1 and Lactated Ringer's solution.

13. The injectable composition of claim 12, wherein the concentration of the anthracycline compound in the injectable composition is from about 0.1 mg/ml to about 25 mg/ml.

14. The injectable composition of claim 12, wherein the concentration of the anthracycline compound in the injectable composition is from about 7 mg/ml to about 17 mg/ml.

15. The injectable composition of claim 12, wherein the concentration of the anthracycline compound in the injectable composition is from about 0.1 mg/ml to about 5 mg/ml.

16. The injectable composition of claim 15, wherein the concentration of the anthracycline compound in the injectable composition is from about 0.25 mg/ml to about 4.5 mg/ml.

17. The injectable composition of claim 16, wherein the concentration of the anthracycline compound in the injectable composition is about 2.4 mg/ml.

18. A method for treating cancer in a patient, comprising administering the reconstituted formulation of claim 1 to the patient.

19. The method of claim 18, wherein the reconstituted formulation is administered intravenously.

20. The method of claim 18, wherein the cancer is selected from: a solid tumor cancer, breast cancer, lung cancer, endometrial cancer, ovarian cancer, pancreatic cancer, cancer of the adrenal cortex, non-Hodgkin's lymphoma, multiple myeloma, leukemia, Kaposi's sarcoma, Ewing's sarcoma, soft tissue sarcoma, nephroblastoma, glioblastoma, prostate cancer, liver cancer, bone cancer, chondrosarcoma, renal cancer, bladder cancer, and gastric cancer.

21. The method according to claim 20, wherein the cancer is selected from:
a solid tumor cancer and a soft tissue sarcoma.

22. The method according to claim 20, wherein the pancreatic cancer is pancreatic ductal adenocarcinoma.

23. A method for treating cancer in a patient, comprising administering the injectable composition of claim 12 to the patient.

24. The method of claim 23, wherein the injectable composition is administered intravenously.

25. The method of claim 23, wherein the cancer is selected from: a solid tumor cancer, breast cancer, lung cancer, endometrial cancer, ovarian cancer, pancreatic cancer, cancer of the adrenal cortex, non-Hodgkin's lymphoma, multiple myeloma, leukemia, Kaposi's sarcoma, Ewing's sarcoma, soft tissue sarcoma, nephroblastoma, glioblastoma, prostate cancer, liver cancer, bone cancer, chondrosarcoma, renal cancer, bladder cancer, and gastric cancer.

26. The method according to claim 25, wherein the cancer is selected from: a solid tumor cancer and a soft tissue sarcoma.

27. The method according to claim 25, wherein the pancreatic cancer is pancreatic ductal adenocarcinoma.

28. A method of preparing the reconstituted formulation of claim 1, comprising reconstituting a lyophilized composition of the anthracycline compound in a reconstitution liquid comprising ethanol and water.

29. The method of claim 28, wherein the volume:volume ratio of ethanol:water is about 10:90 to about 90:10.

30. The method of claim 29, wherein the volume:volume ratio of ethanol:water is about 40:60 to about 60:40.

31. The method of claim 30, wherein the volume:volume ratio of ethanol:water is about 45:55 to about 55:45.

32. The method of claim 31, wherein the volume:volume ratio of ethanol:water is about 50:50.

33. The method of claim 28, wherein the concentration of the anthracycline compound in the reconstituted formulation is from about 1 mg/ml to about 30 mg/ml.

34. The method of claim 33, wherein the concentration of the anthracycline compound in the reconstituted formulation is from about 5 mg/ml to about 25 mg/ml.

35. The method of claim 34, wherein the concentration of the anthracycline compound in the reconstituted formulation is about 10 mg/ml.

36. A method of preparing an injectable composition of an anthracycline compound comprising diluting the reconstituted formulation of claim 1 with Lactated Ringer's solution.

37. The method of claim 36, wherein the concentration of the anthracycline compound in the injectable composition is from about 1 mg/ml to about 25 mg/ml.

38. The method of claim 37, wherein the concentration of the anthracycline compound in the injectable composition is from about 1 mg/ml to about 5 mg/ml.

39. The method of claim 38, wherein the concentration of the anthracycline compound in the injectable composition is from about 7 mg/ml to about 17 mg/ml.

* * * * *